US00PP17156P3

(12) United States Plant Patent
Ichiba

(10) Patent No.: US PP17,156 P3
(45) Date of Patent: Oct. 17, 2006

(54) ***COSMOS* PLANT NAMED 'CACAO CHOCO SANSE 35'**

(50) Latin Name: ***Cosmos astrosanguineus*×*C. sulphureus***
Varietal Denomination: Cacao Choco Sanse 35

(75) Inventor: Kaori Ichiba, Yamanashi (JP)

(73) Assignee: Miyoshi & Co., Ltd., Tokyo (JP)

( * ) Notice: Subject to any disclaimer, the term of this patent is extended or adjusted under 35 U.S.C. 154(b) by 16 days.

(21) Appl. No.: 11/031,823

(22) Filed: Jan. 6, 2005

(65) Prior Publication Data

US 2005/0160509 P1 Jul. 21, 2005

(30) Foreign Application Priority Data

Jan. 21, 2004 (JP) ..... 16582

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

2005/0160508 P1 * 7/2005 Ichiba ..... Plt./226
2005/0160509 P1 * 7/2005 Ichiba ..... Plt./226

OTHER PUBLICATIONS

UPOV ROM GTITM Computer Database, GTI Jouve Retrieval Software 2005/03 Citation for 'Cacao Choco Sanse 35'.*

* cited by examiner

*Primary Examiner*—Kent Bell
*Assistant Examiner*—W C Haas
(74) *Attorney, Agent, or Firm*—Christie, Parker & Hale, LLP

(57) ABSTRACT

A new and distinct variety of *Cosmos,* named 'Cacao Choco Sanse 35', characterized by a very vigorous branching habit, abundance of flowers, high hardiness with high heat resistance, low susceptibility to powdery mildew and mites, large flower size, delayed bloom after pinching and distinctive red color of the flower.

15 Drawing Sheets

RELATED APPLICATIONS

This application claims priority to Japanese PVR Application No. 16582 filed Jan. 21, 2004, the entire contents of which are incorporated by reference herein.

Botanical classification: *Cosmos astrosanguineus*×*C. sulphureus.*

Cultivar denomination: 'Cacao Choco Sanse 35'.

BACKGROUND OF THE INVENTION

The new variety of *Cosmos* was created in a controlled breeding program by crossing two parents; in particular, by crossing as seed parent *Cosmos atrosanguineus* (unpatented) and as pollen parent *Cosmos sulphureus* (unpatented). The breeding program was conducted in Kubuchizawa, Kitakoma-gun, Yamanashi, Japan. The crossing was made in March 2002, and seedlings were transplanted and pinched in early September of the same year. With applied lighting, the first flowers were observed in December 2002 and initial selections were made for new flower color and more vigorous growth. Root cuttings obtained from selected seedlings were planted in September 2003, and final selections for new color and more vigorous growth were made in December 2003.

The resulting seedling of the new variety was grown and asexually propagated by rooted cuttings in Yamanashi, Japan, in March 2004. This propagation and subsequent testing has demonstrated that the combination of traits disclosed herein which characterize the new variety are fixed and retained true to type through successive generations of asexual reproduction.

SUMMARY OF THE INVENTION

The present invention relates to a new and distinct *Cosmos* variety. The varietal denomination of the new variety is 'Cacao Choco Sanse 35'. Among the characteristics which appear to distinguish the new variety from other varieties are a very vigorous branching habit, abundance of flowers, high hardiness with high heat resistance, low susceptibility to powdery mildew and mites, large flower size, delayed bloom after pinching and distinctive red color of the flower.

COMPARISON TO CLOSEST VARIETY

The new variety is closest to *Cosmos atrosanguineus,* but is distinguished therefrom by the following characteristics possessed by 'Cacao Choco Sanse 35' which are different than, or not possessed by, *C. atrosanguineus:*

- Very vigorous branching habit (8 to 10 branches per plant compared to 4 to 5 branches for *C. atrosanguineus*)
- Abundance of flowers (8 to 10 flowers per plant compared to 4 to 5 flowers for *C. atrosanguineus*)
- Rapid growth and establishment (Diameter 10 to 15 cm, thirty days after planting, compared to 8 to 10 cm, thirty days after planting, for *C. atrosanguineus*)
- Distinctive red color of the flower (both have a grayed purple color near RHS 187A, but 'Cacao Choco Sanse 35' has a more reddish color than *C. atrosanguineus*)

Different flowering time (90 to 100 days after pinching, compared to 60 to 70 days after pinching for *C. atrosanguineus*).

PARENT VARIETY COMPARISON

Female parent: *C. atrosanguineus*.

The new variety differs from the female parent in the following characteristics:

1. Much more vigorous branching habit
2. Greater number of flowers per plant
3. Different leaf shape
4. Greater heat tolerance; plants grow over summer without dying. Also, more tolerant to powdery mildew and mites.
5. Flower color is a bit more reddish than that of the female parent.

Male parent: *C. sulphureus*.

The new variety differs from the male parent in the following characteristics:

1. The male parent is annual while 'Cacao Choco Sanse 35' is perennial.
2. Male parent flower color is orange while 'Cacao Choco Sanse 35' has dark red flowers.
3. 'Cacao Choco Sanse 35' has more branches (8–10 branches per plant) than the male parent (3–5 branches per plant).
4. Flower shape is different.
5. Leaf shape is different.

BRIEF DESCRIPTION OF ILLUSTRATIONS

DESCRIPTION OF THE NEW VARIETY

The following detailed description of the new variety is based upon observations taken of plants grown outdoors in 30-cm pots in Kubuchizawa, Kitakoma-gun, Yamanashi, Japan, with a range of day temperatures from 18° to 28° Celsius, and a range of night temperatures from 10° to 18° Celsius.

The following description is in accordance with UPOV terminology and the color terminology herein is in accordance with The Royal Horticultural Society Colour Chart (R.H.S.). The color descriptions and other phenotypical descriptions may deviate from the stated values and descriptions depending upon variation in environmental, seasonal, climatic and cultural conditions.

Plant: When grown at a temperature between −3° and 30° Celsius, the new variety can be grown as perennial.

Figure 1:
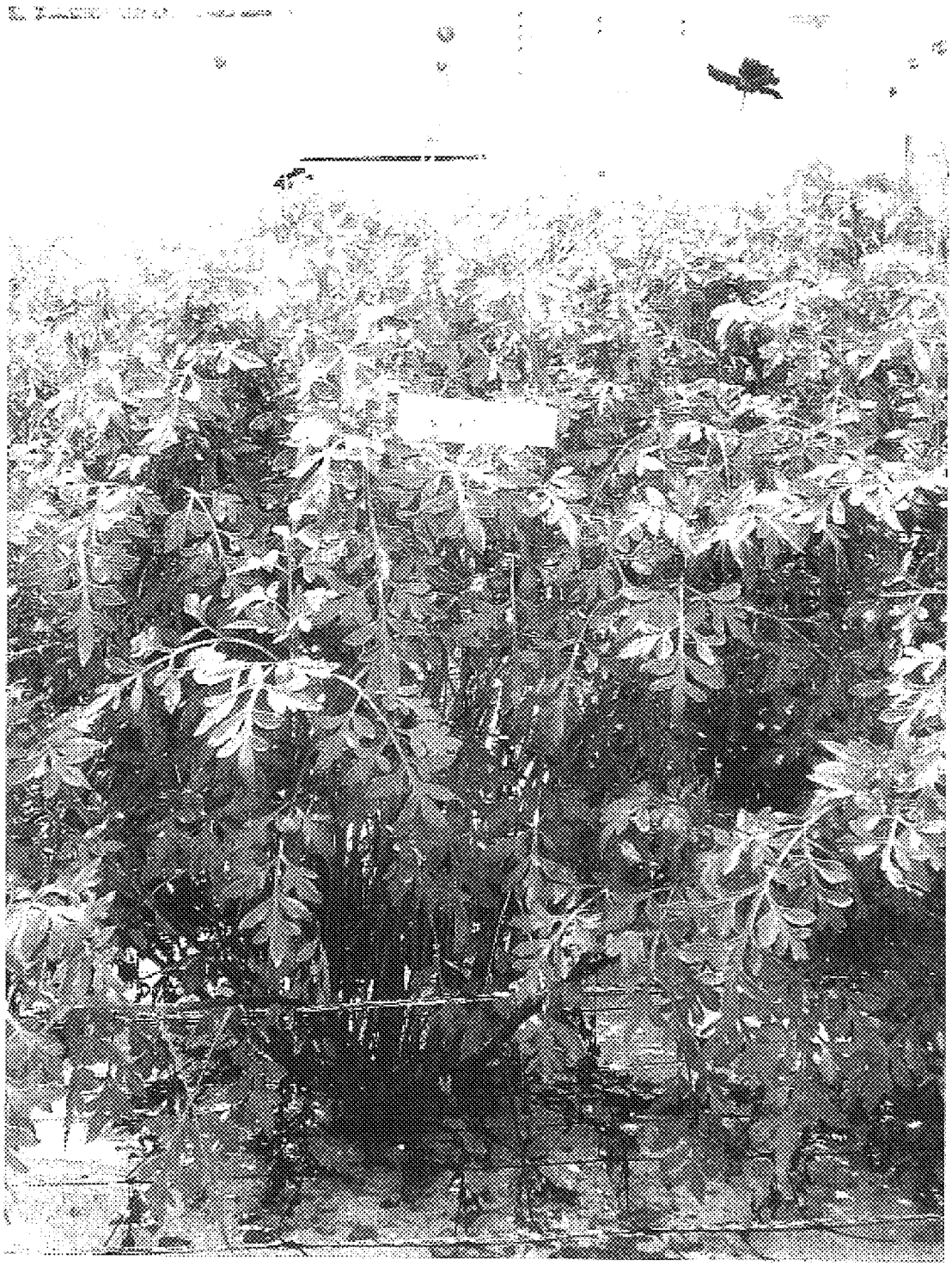
FIG. 1 shows a plant of the new variety.

*Shape.*—Spreading or clump forming, as shown in FIG. 1.

*Height.*—About 30 to 40 cm.

*Diameter.*—About 20 to 25 cm.

*Growth rate.*—Grows to about 25 to 30 cm in two months after planting in soil.

Roots:

*Time to initiate.*—About 30 days.

Figure 2:
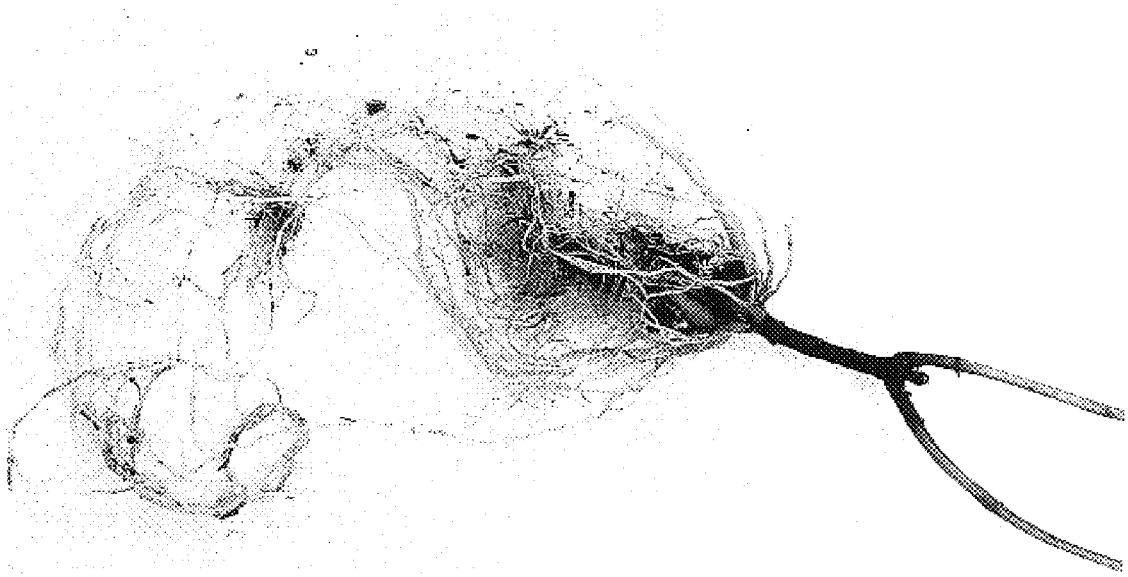
FIG. 2 shows the roots of the new variety.
Figure 17:
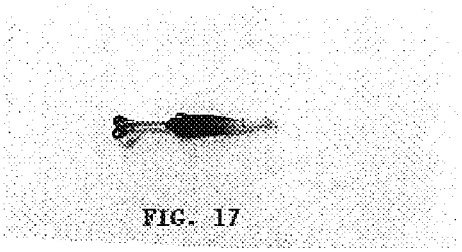
FIG. 17 shows a stigma of the new variety.

*Form.*—Tuberculate, as shown in FIG. 2.

Branches:

*Habit.*—Many branches, with about 8 to 10 lateral branches per plant; stems are hard.

*Length.*—About 30 to 40 cm.

*Diameter.*—About 5 to 8 mm.

*Internode length.*—About 3 to 5 cm.

*Color.*—Grayed purple group, near R.H.S. 187B.

*Pubescence.*—Present.

Figure 3:
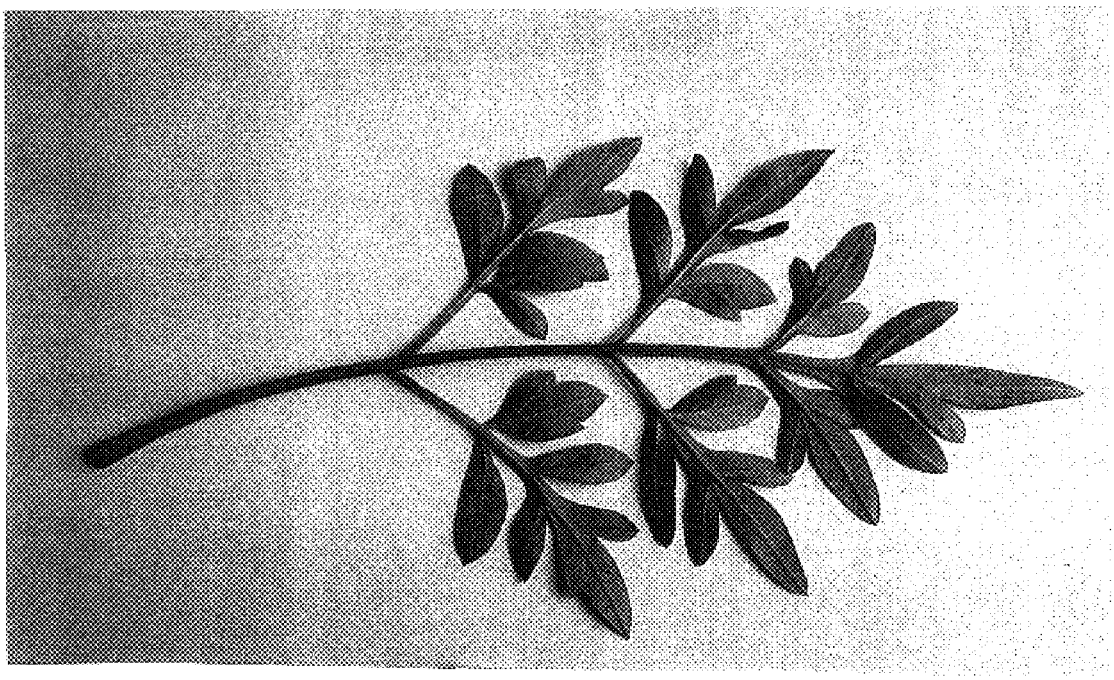
FIG. 3 shows the underside of a leaf of the new variety.
Figure 4:
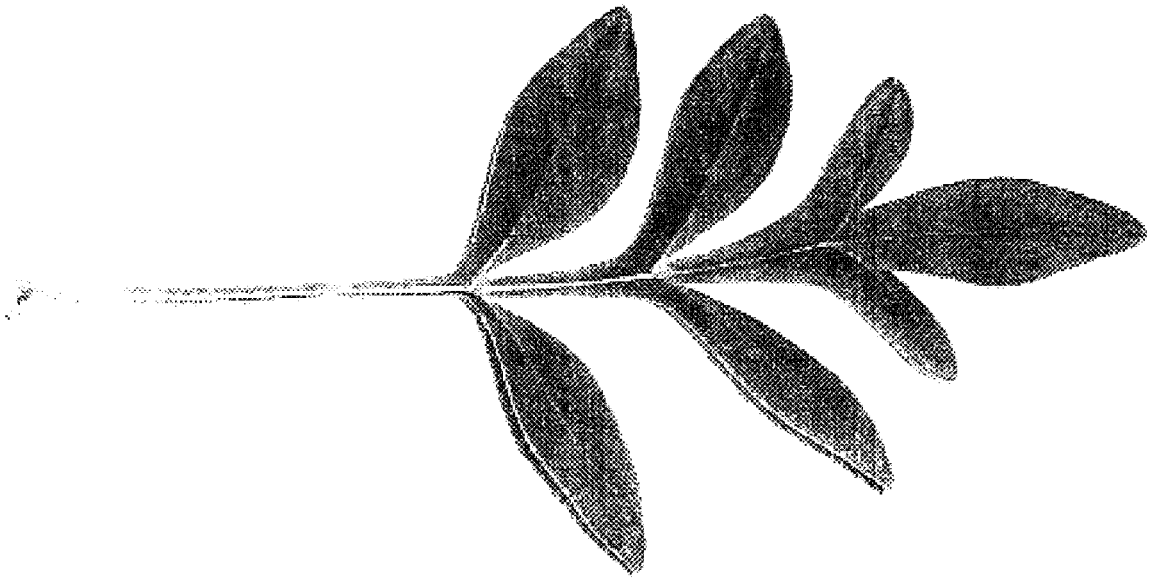
FIG. 4 shows the upperside of a leaflet of the new variety.
Figure 5:
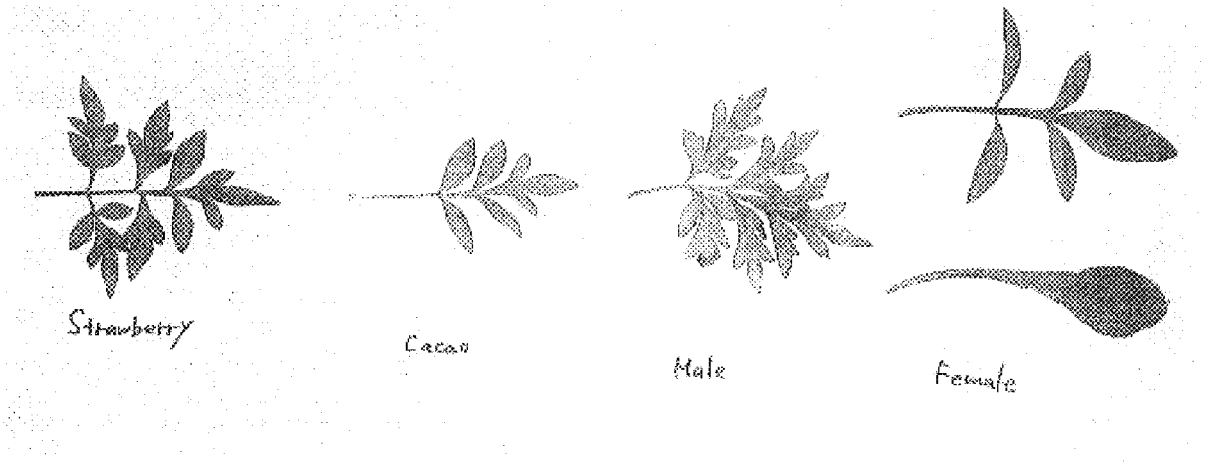
FIG. 5 shows the leaf of the new variety compared to leaves of the male and female parent and the variety 'Strawberry Choco Sanse 41' (U.S. Plant patent application Publication No. 2005/01460508 P1).
Figure 6:
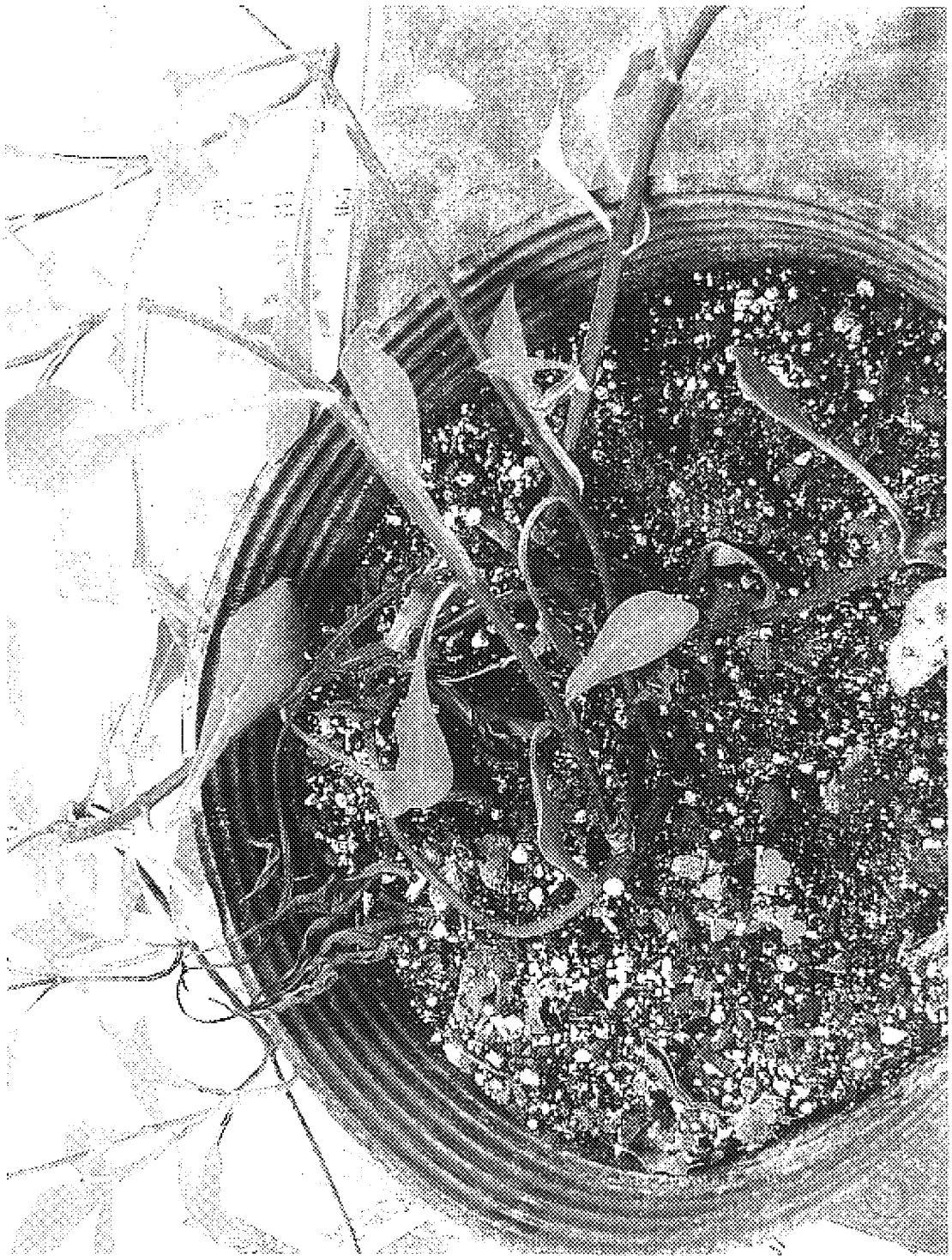
FIG. 6 shows a plant of the female parent *C. atrosanguineus*.
Figure 7:
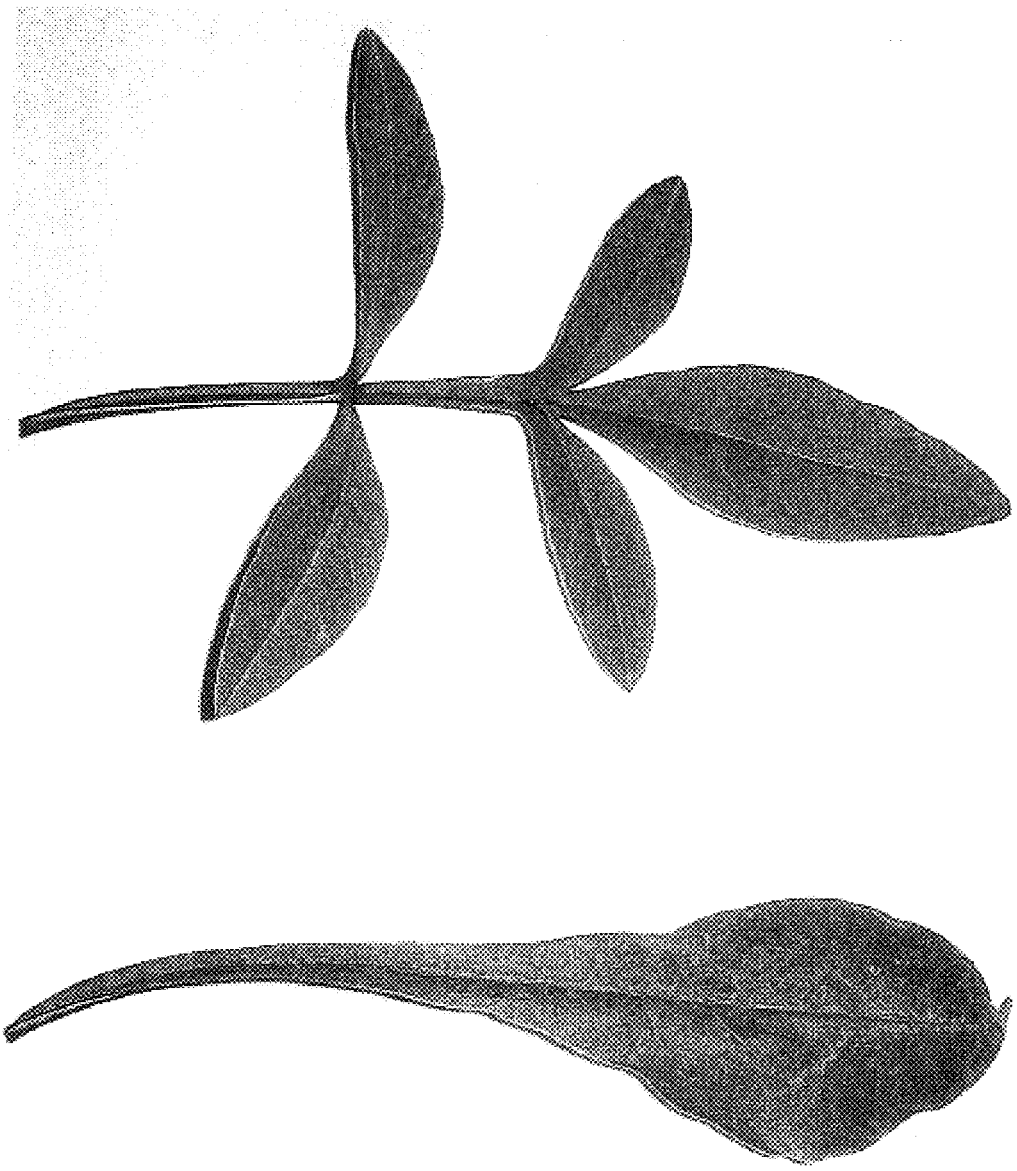
FIG. 7 shows the upperside of a leaf of the female parent *C. atrosanguineus*.
Figure 8:
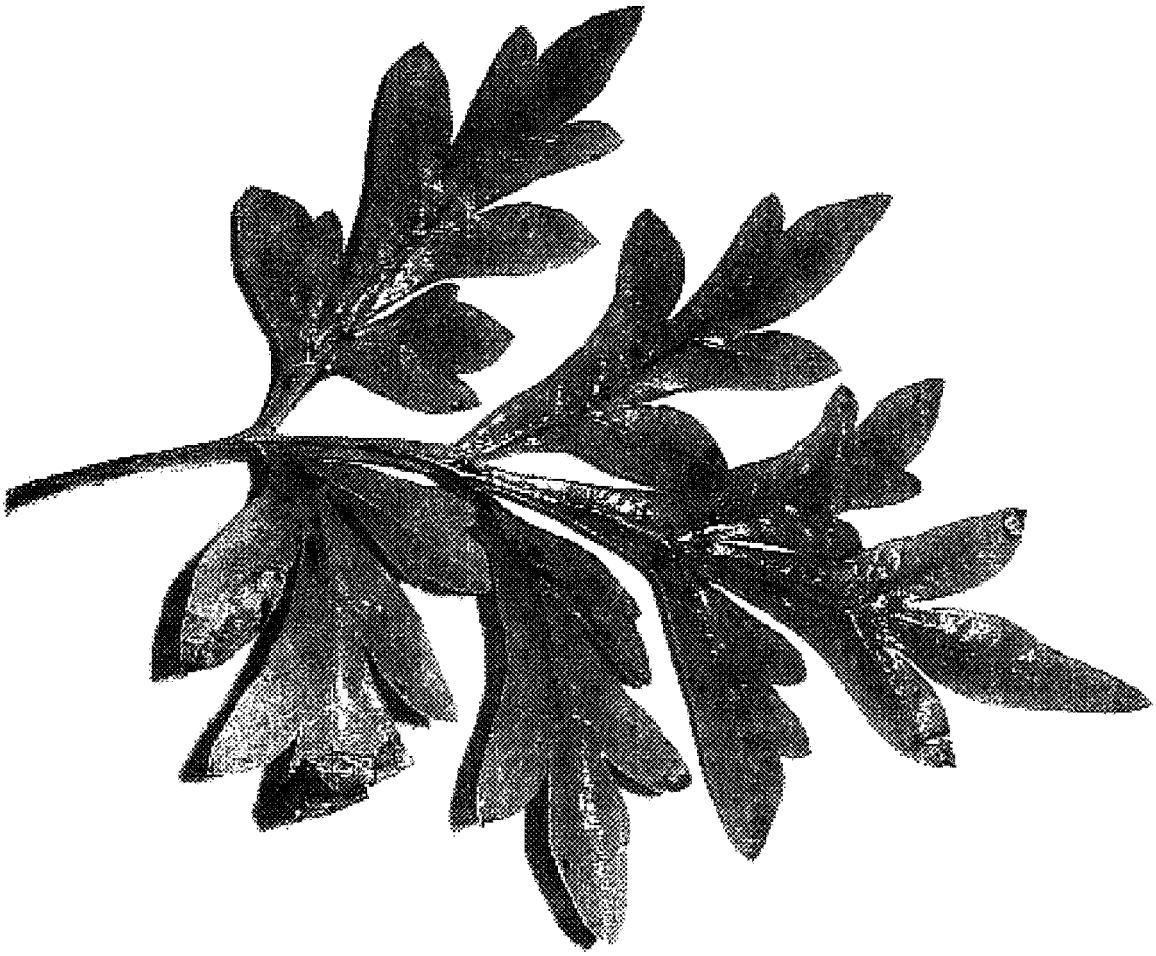
FIG. 8 shows the upperside of a leaf of the male parent *C. sulphureus*.
Figure 9:
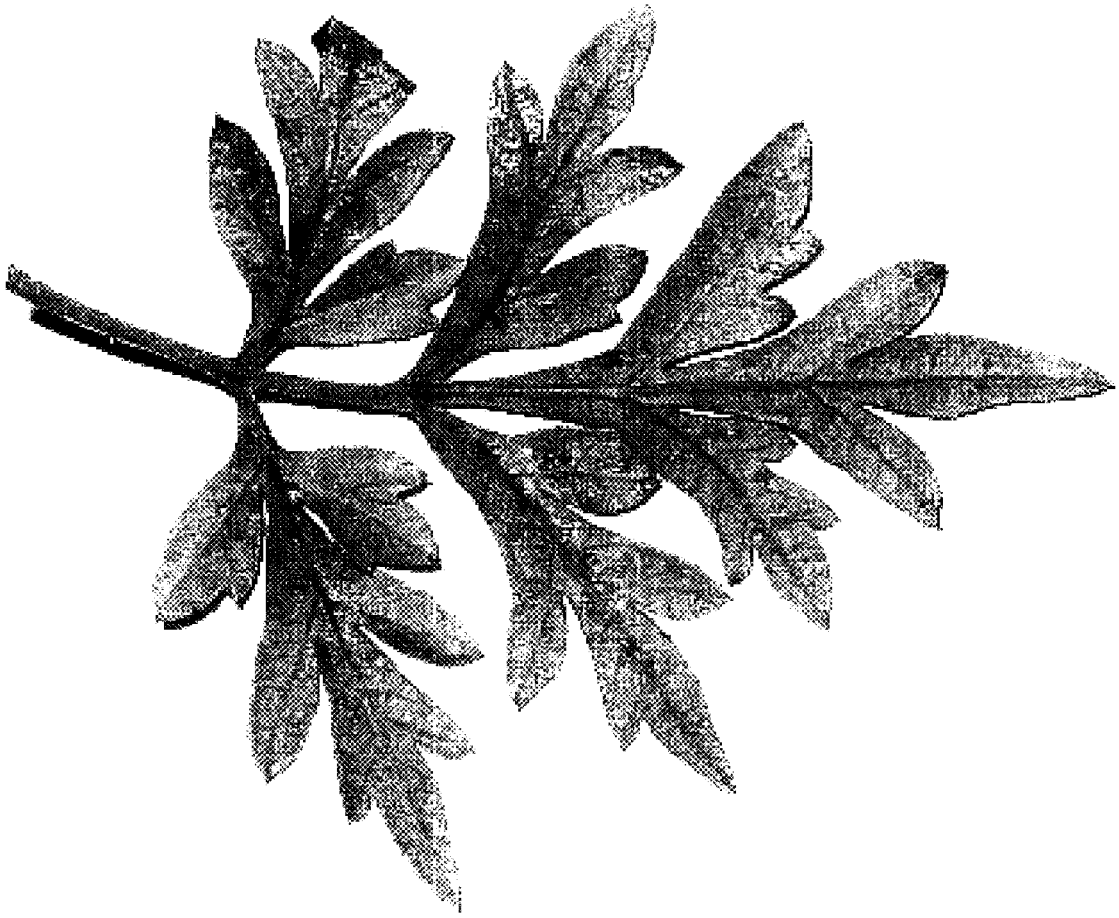
FIG. 9 shows the underside of a leaf of the male parent *C. sulphureus*.
Figure 10:
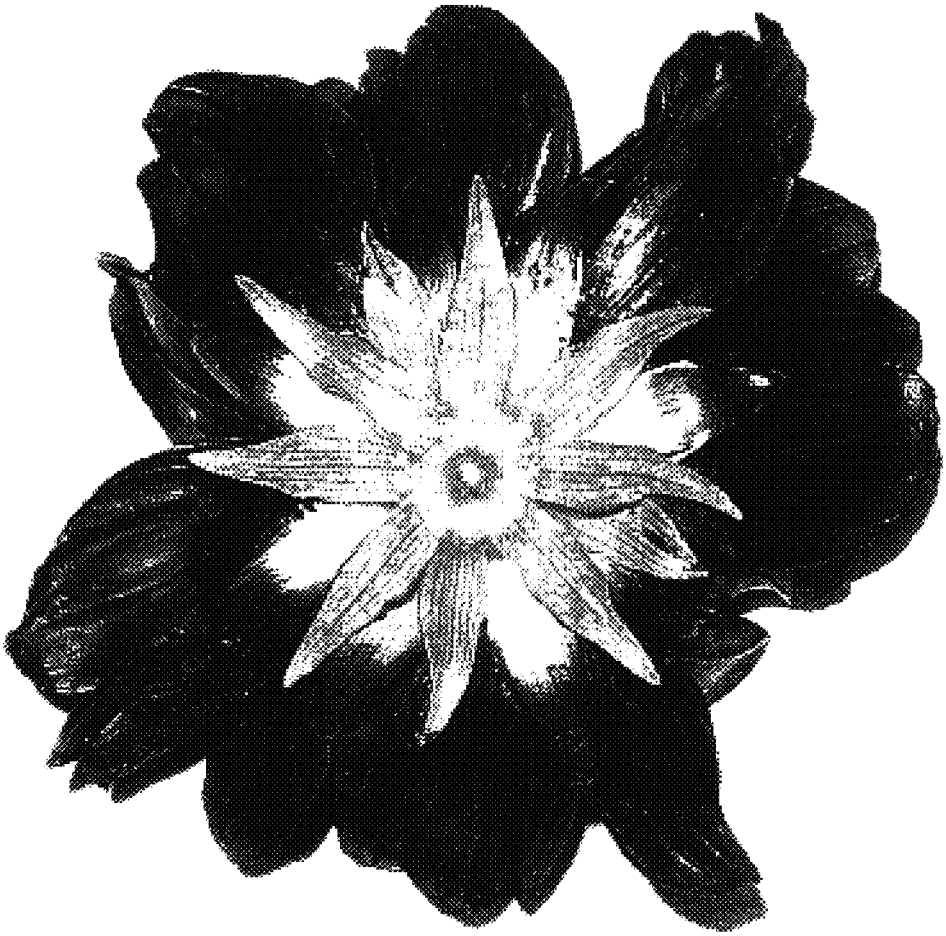
FIG. 10 shows the calyx of the new variety.
Figure 11:
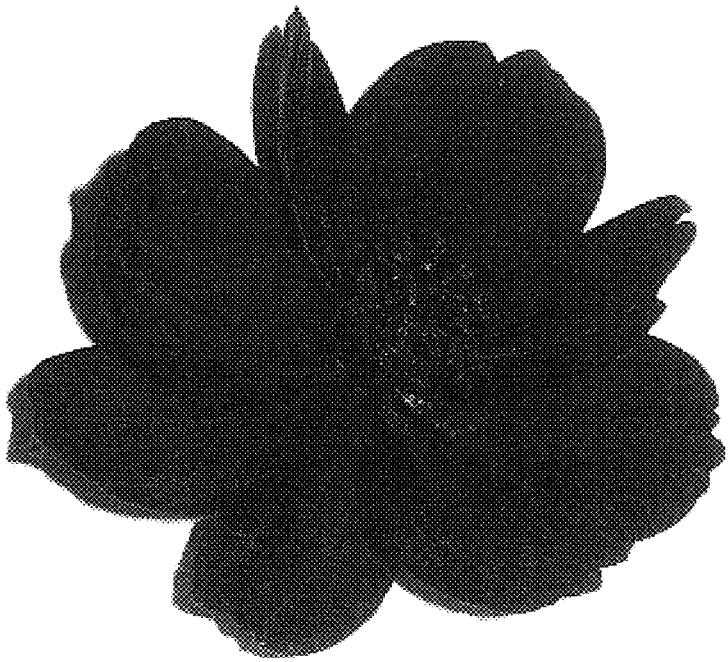
FIG. 11 shows the corolla of the new variety.
Figure 12:
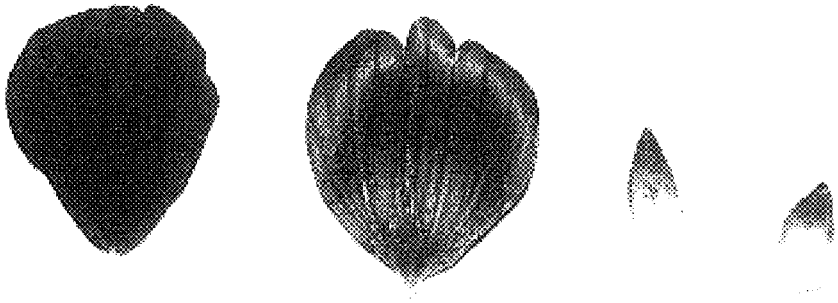
FIG. 12 shows petals of the new variety.
Figure 13:
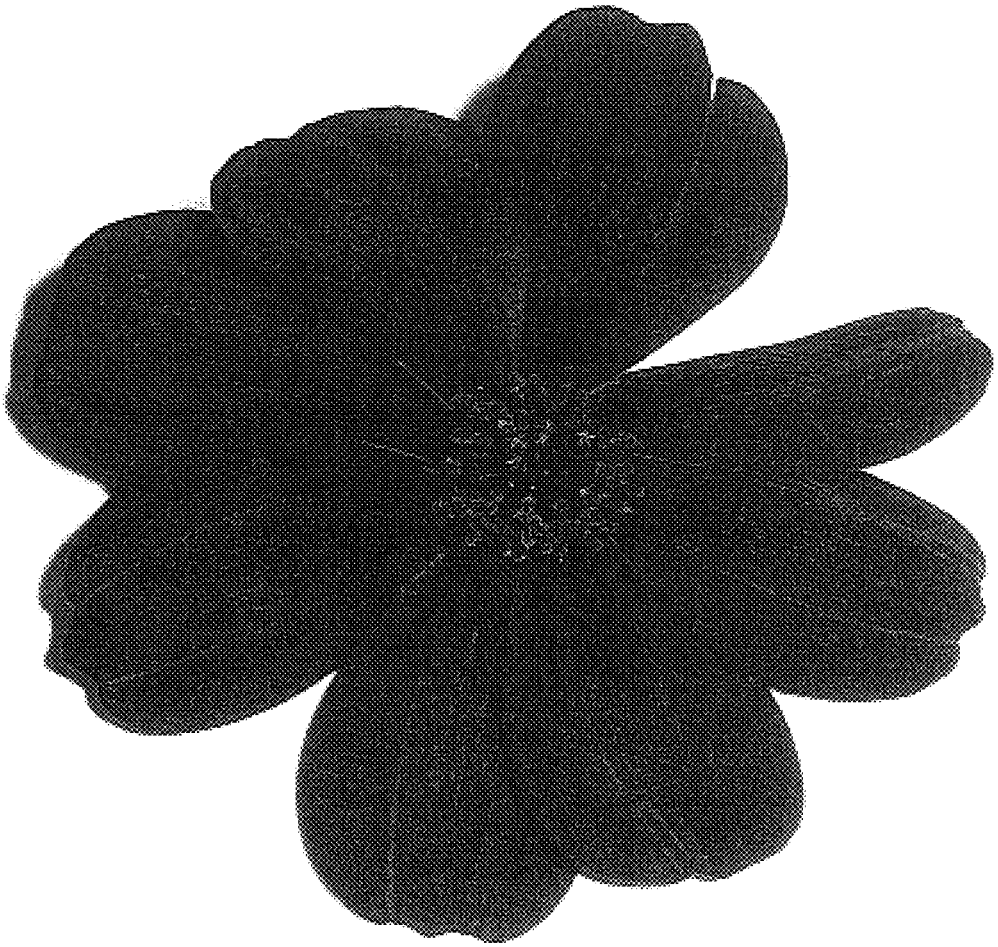
FIG. 13 shows the corolla of the female parent, *C. atrosanguineus,* of the new variety.
Figure 14:
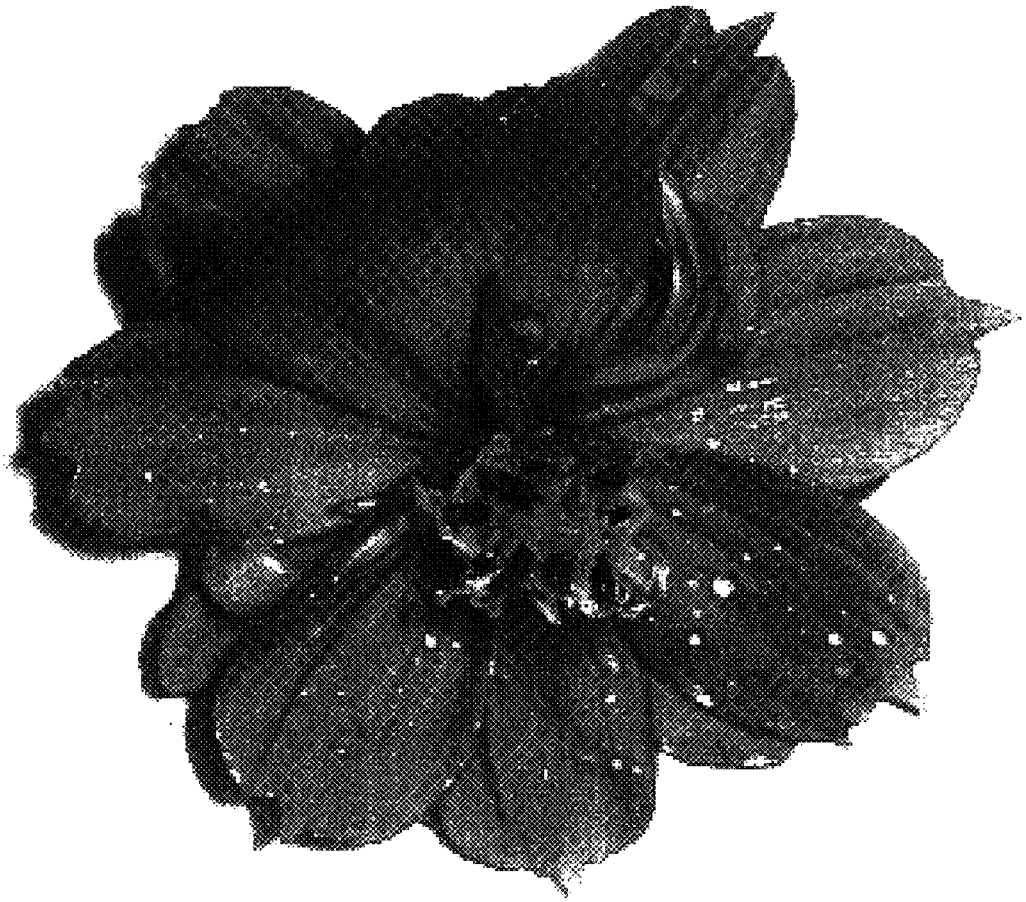
FIG. 14 shows the corolla of the male parent, *C. sulphureus,* of the new variety.
Figure 15:
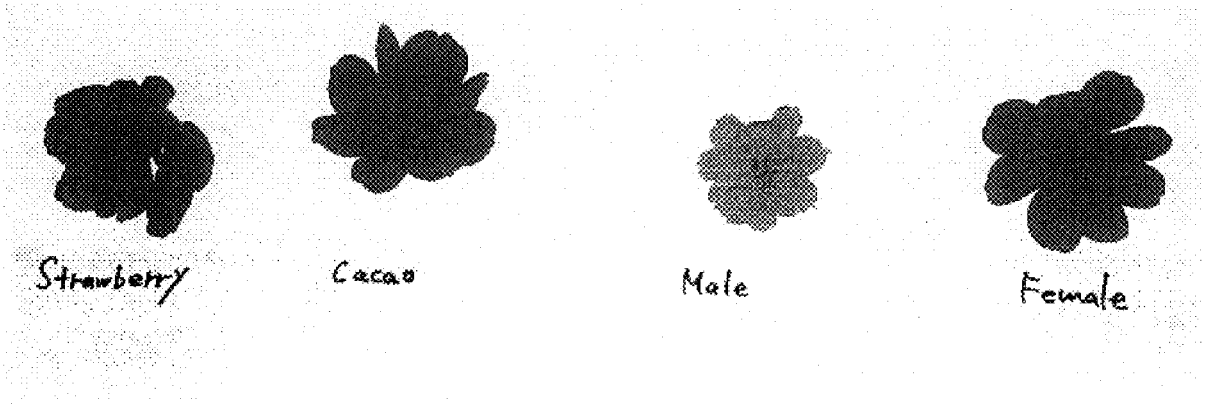
FIG. 15 shows the corolla of the new variety compared to corolla of the male and female parent and the variety 'Strawberry Choco Sanse 41'.
Figure 16:
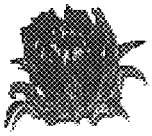
FIG. 16 shows a bud of the new variety compared to a bud of the variety 'Strawberry Choco Sanse 41'.
Figure 16:
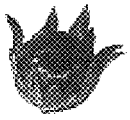

Foliage:

*Leaf arrangement.*—Decussate opposite, as shown in FIG. 3.

*Number.*—About 8 to 12 leaves per lateral branch.

*Form.*—Compound, with 5 leaflets per leaf.

*Leaflet shape.*—Dissected, with acute tip and attenuate base.

*Size.*—About 8 to 10 cm in length, about 4 to 6 cm in width.

*Texture.*—Opaque, not glossy, with some pubescence on the underside.

*Margin.*—Entire.

*Venation.*—Palmate.

*Color, young.*—Upperside, Yellow green group, near R.H.S. 144B; underside, Yellow green group, near R.H.S. 144C.

*Color, mature.*—Upperside, Yellow green group, near R.H.S. 144A; underside, Yellow green group, near R.H.S. 144B.

*Vein color.*—Upperside, Grayed purple group, near R.H.S. 187B; underside, Grayed purple group, near R.H.S. 187B, but slightly lighter than upperside.

*Petiole size.*—Length, about 1.5 to 3.0 cm; diameter, about 3 to 5 mm.

*Petiole color.*—Light reddish brown, near Grayed purple group R.H.S. 187C.

Flower:

*Arrangement.*—Solitary.

*Form.*—Cup shaped.

*Flowering habit.*—Long day plant, normally flowering in June and July.

*Time to flower.*—About 90 to 100 days after pinching.

*Number.*—One flower per lateral stem; 2 to 4 buds per lateral stem; about 13 to 20 flowers and buds per plant.

*Size.*—Diameter, about 5.5 to 6.5 cm; depth, about 1.5 to 2.0 cm.

*Fragrance.*—Soft fragrance.

*Lastingness of bloom.*—On plant, Spring planting, about 120 to 150 days, Autumn planting, about 50 to 90 days; cut flower, about 7 to 10 days.

*Number of petals.*—About 8 to 10 per flower.

*Petal texture.*—Velvety.

*Petal size.*—Length, about 3.0 cm; width, about 2.4 cm.

*Petal color.*—When opening Upperside, Grayed purple group, near R.H.S. 187A, underside, Grayed purple group, near R.H.S. 187A; fully opened Upperside, Grayed purple group, near R.H.S. 187A, underside, Grayed purple group, near R.H.S. 187B.

*Number of sepals.*—About 10 per flower.

*Sepal color.*—Upperside, Green group, near R.H.S. 137C, underside, Green group, near R.H.S. 137C.

*Calyx size.*—Length, about 1.2 to 1.4 cm, diameter, about 2.2 to 2.5 cm.

*Peduncle length.*—About 13 to 18 cm.

*Peduncle color.*—Yellow green group, near R.H.S. 146D.

*Flower bud size.*—Length, about 0.9 to 1.3 cm; diameter, about 0.9 to 1.3 cm.

*Bud opening rate.*—About 70% to 80%.

*Flower bud color.*—Grayed purple group near R.H.S. 187 A.

*Stamen.*—Degenerated.

*Anther.*—Degenerated.

*Pistil.*—Number, about 30 to 50 per flower; length, about 5 to 8 mm.

*Stigma.*—Color, Yellow group, near R.H.S. 13A.

*Style.*—Length, about 0.8 to 1.0 mm; color, Yellow group, near R.H.S. 13A.

*Ovary.*—Color, light yellow, near R.H.S. 154D; no seed development.

Disease resistance: Increased tolerance to powdery mildew and mites.

Heat tolerance: Increased heat tolerance; plants grow over summer without dying.

I claim:

1. A new and distinct variety of *Cosmos* plant, identified as 'Cacao Choco Sanse 35', substantially as shown and described.

* * * * *

Strawberry

CaCao